US012805848B2

(12) United States Patent
Wen et al.

(10) Patent No.: US 12,805,848 B2
(45) Date of Patent: Nov. 24, 2026

(54) ULTRASONIC IMAGING SYSTEM

(71) Applicant: SHENZHEN MINDRAY BIO-MEDICAL ELECTRONICS CO., LTD., Shenzhen (CN)

(72) Inventors: Dayue Wen, Shenzhen (CN); Li Li, Shenzhen (CN); Donghai Qin, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 19/037,467

(22) Filed: Jan. 27, 2025

(65) Prior Publication Data

US 2025/0241625 A1 Jul. 31, 2025

(30) Foreign Application Priority Data

Jan. 30, 2024 (CN) ......................... 202410142195.7

(51) Int. Cl.
*A61B 8/00* (2006.01)

(52) U.S. Cl.
CPC .............. *A61B 8/56* (2013.01); *A61B 8/4272* (2013.01); *A61B 8/4472* (2013.01); *A61B 8/54* (2013.01); *A61B 8/4427* (2013.01)

(58) Field of Classification Search
CPC .................................... A61B 8/54; A61B 8/56
See application file for complete search history.

(56) References Cited

U.S. PATENT DOCUMENTS

| | | | | |
|---|---|---|---|---|
| 8,335,864 B2 * | 12/2012 | Cullimore | ................. | G06F 9/54 718/1 |
| 10,159,465 B2 * | 12/2018 | Pelissier | ................ | A61B 8/465 |
| 2011/0107357 A1 | 5/2011 | Cullimore | | |
| 2014/0114190 A1 | 4/2014 | Noah | | |
| 2016/0278739 A1 | 9/2016 | Kris | | |
| 2024/0307917 A1 * | 9/2024 | Wu | ....................... | B06B 1/0607 |

FOREIGN PATENT DOCUMENTS

| | | | |
|---|---|---|---|
| CN | 110167449 | A | 8/2019 |
| CN | 116233268 | A | 6/2023 |
| CN | 222075222 | U | 11/2024 |
| KR | 20170072533 | A | 6/2017 |

* cited by examiner

*Primary Examiner* — Colin T. Sakamoto
(74) *Attorney, Agent, or Firm* — SYNCODA LLC; Feng Ma

(57) ABSTRACT

Disclosed is an ultrasonic imaging system including an ultrasonic probe, a host control platform and a terminal device. The host control platform includes a programmable logic device, a controller and a second communication interface. The programmable logic device includes a scan control circuit, the controller is deployed with a communication protocol stack. The scan control circuit is configured to control the ultrasonic probe to emit and receive ultrasonic waves. The communication protocol stack is configured to implement the package and transmission of data.

18 Claims, 5 Drawing Sheets

ULTRASONIC IMAGING SYSTEM

CROSS-REFERENCE TO RELATED APPLICATION

This application claims priority to Chinese patent Application No. 202410142195.7 filed on Jan. 30, 2024, the disclosure of which is hereby incorporated by reference in its entirety.

TECHNICAL FIELD

The present disclosure relates to medical devices, in particular to ultrasonic imaging systems.

BACKGROUND

Traditional ultrasonic devices mainly fall into two major categories, namely desktop ultrasonic devices and portable ultrasonic devices. Desktop ultrasonic devices are large in size but offer high imaging quality, making them suitable for fixed usage locations. Portable ultrasonic devices, resembling laptops in appearance and smaller in size, can be more easily transported to other locations for use.

However, traditional portable ultrasonic devices are still relatively large and inconvenient to carry around. Moreover, as the ultrasonic devices become more compact, they tend to consume more power and have a longer startup time, which adversely affects the user experience.

SUMMARY

In some embodiments, an ultrasonic imaging system provided may include:

- an ultrasonic probe;
- a terminal device including a first communication interface; and
- a host control platform configured to control the ultrasonic probe to emit
- ultrasonic waves to an object under examination and receive ultrasonic echoes so as to obtain ultrasonic data, and transmit the ultrasonic data to the terminal device;
- wherein the host control platform may include:
- a programmable logic device including a scan control circuit that is configured to control the ultrasonic probe to emit ultrasonic waves to the object under examination and receive ultrasonic echoes so as to obtain ultrasonic data;
- a second communication interface that is capable of establishing a communication connection with the first communication interface; and
- a controller, wherein the controller is deployed with a dedicated operating system and communication protocol stack, the dedicated operating system is a simplified operating system for controlling communication between the programmable logic device and the terminal device, the communication protocol stack is compatible with the second communication interface, and the dedicated operating system is configured to obtain the ultrasonic data from the programmable logic device, invoke the communication protocol stack into packet data conforming to a communication protocol corresponding to the communication protocol stack, and transmit the packet data to the terminal device via the second communication interface.

In some embodiments, the communication protocol stack may include a TCP protocol stack and a WIFI protocol stack; and/or

- the communication protocol stack may include a TCP protocol stack and a Bluetooth protocol stack; and/or
- the communication protocol stack may include a USB protocol stack; and/or
- the communication protocol stack may include a SPI protocol stack; and/or
- the communication protocol stack may include a SDIO protocol stack; and/or
- the communication protocol stack may include a RMII protocol stack.

In some embodiments, the second communication interface may include at least one of a WIFI communication interface, a Bluetooth communication interface, a SPI communication interface, a SDIO communication interface, a RMII communication interface and a USB communication interface.

In some embodiments, the USB communication interface may support a control transfer mode, an interrupt transfer mode, a bulk transfer mode and an isochronous transfer mode, and the USB communication interface may utilize the bulk transfer mode or the isochronous transfer mode to transmit the packet data.

In some embodiments, the programmable logic device may be without an ARM core or without a deployed protocol stack.

In some embodiments, the programmable logic device may be an FPGA.

In some embodiments, the host control platform may be arranged within the ultrasonic probe; or

- the ultrasonic probe and the host control platform may be connected to form an integrated structure; or
- the host control platform may be provided with a socket, and the ultrasonic probe may be detachably connected to the host control platform.

In some embodiments, the host control platform may be connected to the ultrasonic probe via a wired or wireless connection.

In some embodiments, the terminal device may include at least one of a smartphone, a tablet computer, a cloud server and an ultrasonic imaging apparatus.

In some embodiments, the programmable logic device may further include a data processing circuit configured to process the ultrasonic data.

In some embodiments, the data processing circuit may include a beamforming circuit configured to perform at least partial beamforming on the ultrasonic data.

In some embodiments, the data processing circuit may further include a signal processing circuit configured to process the beamformed ultrasonic data to obtain an ultrasonic image.

In some embodiments, the data processing circuit may further include an image processing circuit configured to process the obtained ultrasonic image.

In some embodiments, the host control platform may further include a data processing device configured to process the ultrasonic data.

In some embodiments, the data processing device may include a beamformer configured to perform at least partial beamforming on the ultrasonic data.

In some embodiments, the data processing device may further include a processor configured to process the beamformed ultrasonic data to obtain an ultrasonic image.

In some embodiments, the processor may be further configured to process the obtained the ultrasonic image.

In some embodiments, the second communication interface comprises a port physical layer, wherein the second communication interface or the port physical layer is integrated with the controller.

In some embodiments, an ultrasonic imaging system provided may include:

an ultrasonic probe;

a programmable logic device including a scan control circuit that is configured to control the ultrasonic probe to emit ultrasonic waves to an object under examination and receive ultrasonic echoes so as to obtain ultrasonic data;

a second communication interface capable of establishing a communication connection with a target device; and a controller deployed with a dedicated operating system and a communication protocol stack, wherein the dedicated operating system is a simplified operating system for controlling communication between the programmable logic device and the target device, the communication protocol stack is a communication protocol stack that is compatible with the second communication interface, and the dedicated operating system is configured to obtain the ultrasonic data from the programmable logic device, invoke the communication protocol stack to convert the ultrasonic data into packet data conforming to a communication protocol corresponding to the communication protocol stack, and transmit the packet data to the target device via the second communication interface.

In some embodiments, an ultrasonic imaging system provided may include:

an ultrasonic probe;

a scan control circuit configured to control the ultrasonic probe to emit ultrasonic waves to an object under examination and receive ultrasonic echoes so as to obtain ultrasonic data;

a second communication interface capable of establishing a communication connection with a target device; and a controller deployed with a dedicated operating system and a communication protocol stack, wherein the dedicated operating system is a simplified operating system for controlling communication between the scan control circuit and the target device, the communication protocol stack is a communication protocol stack that is compatible with the second communication interface, and the dedicated operating system is configured to obtain the ultrasonic data from the scan control circuit, invoke the communication protocol stack to convert the ultrasonic data into packet data conforming to a communication protocol corresponding to the communication protocol stack, and transmit the packet data to the target device via the second communication interface.

In some embodiments, an ultrasonic imaging system is provided, which may include:

an ultrasonic probe;

a terminal device, including a first communication interface; and a host control platform, configured to control the ultrasonic probe to emit ultrasonic waves to an object under examination and receive ultrasonic echoes to obtain ultrasonic data, and transmit the ultrasonic data to the terminal device;

where the host control platform includes:

a programmable logic device, including a scan control circuit that is configured to control the ultrasonic probe to emit the ultrasonic waves to the object under examination and receive the ultrasonic echoes to obtain the ultrasonic data;

a second communication interface, capable of establishing a communication connection with the first communication interface; and a controller, deployed with a communication protocol stack, wherein, the communication protocol stack is compatible with the second communication interface, and the controller is configured to obtain the ultrasonic data from the programmable logic device, invoke the communication protocol stack to convert the ultrasonic data into packet data that conforms to a communication protocol corresponding to the communication protocol stack, and transmit the packet data to the terminal device via the second communication interface.

In some embodiments, an ultrasonic imaging system is provided, which may include:

an ultrasonic probe;

a programmable logic device, including a scan control circuit that is configured to control the ultrasonic probe to emit ultrasonic waves to an object under examination and receive ultrasonic echoes so as to obtain ultrasonic data;

a second communication interface, capable of establishing a communication connection with a target device; and a controller, deployed with a communication protocol stack, wherein, the communication protocol stack is compatible with the second communication interface, and the controller is configured to obtain the ultrasonic data from the programmable logic device, invoke the communication protocol stack to convert the ultrasonic data into packet data that conforms to a communication protocol corresponding to the communication protocol stack, and transmit the packet data to the target device via the second communication interface.

In some embodiments, an ultrasonic imaging system is provided, which may include:

an ultrasonic probe;

a scan control circuit, configured to control the ultrasonic probe to emit ultrasonic waves to an object under examination an receive ultrasonic echoes so as to obtain ultrasonic data;

a second communication interface, capable of establishing a communication connection with a target device; and a controller, deployed with a communication protocol stack, wherein, the communication protocol stack is compatible with the second communication interface, and the controller is configured to obtain the ultrasonic data from the scan control circuit, invoke the communication protocol stack to convert the ultrasonic data into packet data that conforms to a communication protocol corresponding to the communication protocol stack, and transmit the packet data to the target device via the second communication interface.

In some embodiments, the controller is further deployed with an operating system, and the controller obtains the ultrasonic data from the scan control circuit, invokes the communication protocol stack to convert the ultrasonic data into packet data that conforms to a communication protocol corresponding to the communication protocol stack, and transmits the packet data to the target device via the second communication interface through the operating system.

In some embodiments, the operating system is a Linux operating system or an RTOS operating system.

In some embodiments, the second communication interface comprises a port physical layer, wherein the second communication interface or the port physical layer is integrated with the controller.

In some embodiments above, the programmable logic device and the controller are provided, the scan control circuit for controlling the ultrasonic probe to transmit and receive ultrasonic waves is provided in the programmable logic device, and the communication protocol stack is provided in the controller to obtain and transmit data packets. This way, the constraints on the selection of the programmable logic device are reduced. Furthermore, the communication protocol stack is independent of the programmable logic device. Therefore, the programmable logic device does not need to be provided with a communication protocol stack, which allow the use of a conventional FPGA.

In some embodiments above, there is a better design decoupling. The programmable logic device and the controller can be interconnected through the operating system. Maintaining this interconnection allows for changes within either the programmable logic device or the controller without affecting the functional operation of the other.

In some embodiments above, better expansion performance can be achieved. When the ultrasound imaging system needs to improve the imaging performance, a programmable logic device with higher performance can be replaced independently; and similarly, when there are changes or new requirements for the communication interfaces, the first and second communication interfaces can be replaced independently.

In some embodiments above, lower power consumption can be achieved. During the freezing period of ultrasound imaging, the controller can maintain an external communication connection, while the programmable logic device does not need to maintain communication all the time. Therefore, the programmable logic device can be in a low-power standby state, and can be restored to normal operation when the ultrasound imaging scan is performed.

DETAILED DESCRIPTION

Figure 1:
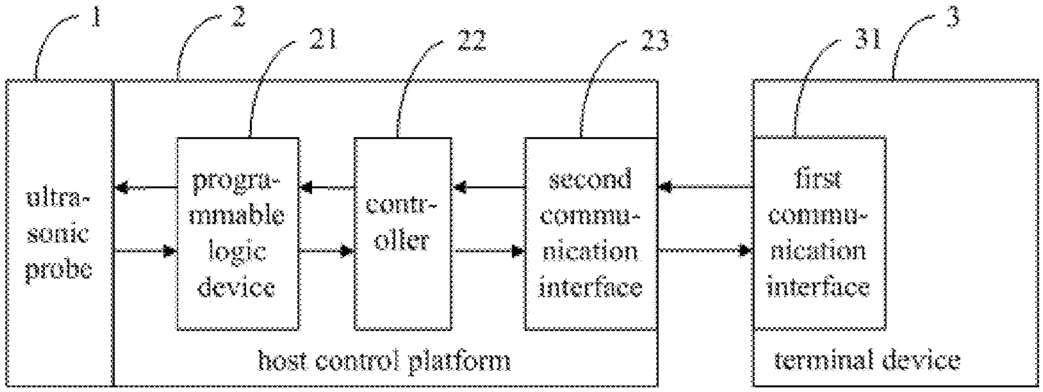
FIG. 1 is a block diagram of an ultrasonic imaging system according to some embodiments.

Handheld ultrasonic imaging system falls under the category of a slave device. It can communicate with terminal devices such as smartphones and front-end hosts via wired or wireless means, with the terminal devices serving as master devices in the communication. The function of the ultrasonic imaging system to package and encapsulate data is typically implemented by using a communication protocol stack, such as WiFi protocol stack, USB protocol stack, and so on. A protocol stack is a specific software function that needs to be deployed into the ARM or MCU chip of the hardware. The deployment of the ARM or MCU chip within the circuit is of great significance, as its placement directly determines the design scheme and interconnection architecture of the entire hardware circuit, as well as the software architecture, ultimately affecting key performance indicators of the entire ultrasonic product (such as size, power consumption, startup time, etc.).

In existing ultrasonic imaging systems, a non-conventional programmable logic chip, namely an FPGA (with an embedded ARM core), is utilized to implement the functionality of the above-mentioned ARM running the communication protocol stack, i.e., using a general-purpose processing chip to execute communication protocol stacks such as WiFi/USB ones. As a result, the programmable logic chip needs to keep operating continuously. When it is not in the imaging scanning process and only needs to maintain external communication, it still cannot achieve low-power operation. This leads to relatively high power consumption of the handheld ultrasonic imaging systems. Moreover, since all functions are integrated within the programmable logic chip, the startup time of the handheld ultrasonic imaging system is rather long.

Based on the above analysis, the present application proposes a novel handheld ultrasonic imaging system. In this device, a combination of conventional programmable logic chips and dedicated control chips is employed to achieve various functions. Specifically, the programmable logic chip is utilized solely for imaging scanning or additionally for image processing, while modules such as the communication protocol stack are implemented within the dedicated chip(s). This approach allows for greater flexibility in the selection of the programmable logic chip, enabling the use of a conventional general-purpose computing chip such as an FPGA. During the freeze period of ultrasonic imaging (when transmission and reception of ultrasonic waves are disabled), the programmable logic device can operate at reduced power consumption or even be powered down completely, with only the dedicated control chip(s) maintaining external communication connections. When imaging scanning is required, the programmable logic device can be restored to normal operation. Furthermore, by distributing different functions between the programmable logic chip and the dedicated control chip(s), the burden on each chip can be reduced, facilitating rapid startup of the ultrasonic imaging system.

The present disclosure will be further described in detail below through specific embodiments with reference to the accompanying drawings. Common or similar elements are referenced with like or identical reference numerals in different embodiments. Many details described in the following embodiments are for better understanding the present disclosure. However, those skilled in the art can realize with minimal effort that some of these features can be omitted in different cases or be replaced by other elements, materials and methods. For clarity some operations related to the present disclosure are not shown or illustrated herein so as to prevent the core from being overwhelmed by excessive descriptions. For those skilled in the art, such operations are not necessary to be explained in detail, and they can fully understand the related operations according to the description in the specification and the general technical knowledge in the art.

In addition, the features, operations or characteristics described in the specification may be combined in any suitable manner to form various embodiments. At the same time, the steps or actions in the described method can also be sequentially changed or adjusted in a manner that can be apparent to those skilled in the art. Therefore, the various sequences in the specification and the drawings are only for the purpose of describing a particular embodiment, and are not intended to be an order of necessity, unless otherwise stated one of the sequences must be followed.

The serial numbers of components herein, such as “first”, “second”, etc., are only used to distinguish the described objects and do not have any order or technical meaning. The terms “connected”, “coupled” and the like here include direct and indirect connections (coupling) unless otherwise specified.

In some embodiments, an ultrasonic imaging system is provided. This ultrasonic imaging system is a compact device designed for handheld use and functions as a slave device. The ultrasonic imaging system is configured to emit ultrasonic waves and receive ultrasonic echoes to obtain ultrasonic data, and then package and encapsulate the ultrasonic data either directly or after processing and send them a terminal device (master device). This ultrasonic imaging system offers advantages such as miniaturization, portability, low power consumption and good scalability, making it suitable for a wide range of applications.

Please refer to FIG. 1. The ultrasonic imaging system in the shown embodiment mainly includes an ultrasonic probe 1, a host control platform 2 and a terminal device 3. The ultrasonic probe 1 is configured to emit and receive ultrasonic waves to obtain ultrasonic data. The host control platform 2 is configured to obtain the ultrasonic data and then package and send it directly or after processing to the terminal device 3. The terminal device 3 is configured to display an ultrasonic image and to control ultrasonic imaging, as well as making settings for ultrasonic imaging.

The ultrasonic probe 1 is provided inside with a transducer. The ultrasonic probe 1 is configured to emit ultrasonic waves to an object under examination and receive ultrasonic echoes reflected by the object under examination, and generate corresponding ultrasonic data based on the received ultrasonic echoes, that is, the ultrasonic probe 1 converts ultrasonic signals into electrical signals.

The host control platform 2 can be connected to the ultrasonic probe 1 via a wired or wireless connection. The host control platform 2 is housed within the ultrasonic probe 1, and together they form an integrated structure. This compact and integrated design facilitates easy carrying and use by users.

In other embodiments, the host control platform 2 is of a small size and can be a module that can be held with one hand. The ultrasonic probe 1 can be integrated with the host control platform 2 to form a handheld integrated device that can be operated with one hand. The ultrasonic probe 1 can also be connected to the host control platform 2 via a cable or a wireless communication module, allowing users to carry the host control platform 2 on their body or in one hand while operating the ultrasonic probe 1 with the other hand. Whether the ultrasonic probe 1 and the host control platform 2 are integrated or separate, they are both designed for convenient use by users.

In other embodiments, an end of the host control platform 2 may also be provided with a socket. The body of the ultrasonic probe 1, either directly or via a cable plug, may be detachably connected to the socket of the host control platform 2. This detachable connection between the ultrasonic probe 1 and the host control platform 2 allows the host control platform 2 to be paired with different ultrasonic probes 1 for ultrasonic imaging, thereby meeting a wider range of application needs.

In the shown embodiment, the terminal device 3 may include at least one of a smartphone, a tablet computer (pad), a cloud server and an ultrasonic imaging apparatus. The ultrasonic imaging apparatus may be a conventional one, such as a traditional desktop ultrasonic imaging apparatus or a traditional portable ultrasonic imaging apparatus.

The terminal device 3 may include a first communication interface 31 configured to communicate with the host control platform 2. The terminal device 3 can send an imaging scanning instruction to the host control platform 2 via the first communication interface 31, and can also receive ultrasonic data via the first communication interface 31.

Figure 2:
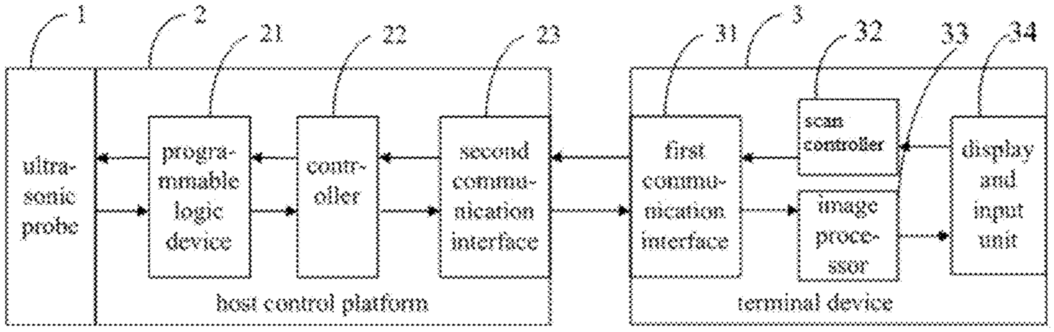
FIG. 2 is a block diagram of an ultrasonic imaging system according to some embodiments.

Please refer to FIG. 2. In other embodiments, the terminal device 3 may further be provided inside with a scan controller 32 and an image processor 33. The scan controller 32 and the image processor 33 may be modules located on a single chip, or they may be two separate chips. The scan controller 32 may be configured to generate and issue an scanning instruction, and the image processor 33 may be configured to receive and process the ultrasonic data.

The terminal device 3 may further include a display and input unit 34. The display and input unit 34 may be an integrated touchscreen; or it may include two separate devices for displaying and input. For example, the input device may be one or more of a control panel, a keyboard and a mouse. The display device may be configured to display ultrasonic image, and the input device may be configured to input an imaging scanning instruction.

Figure 3:
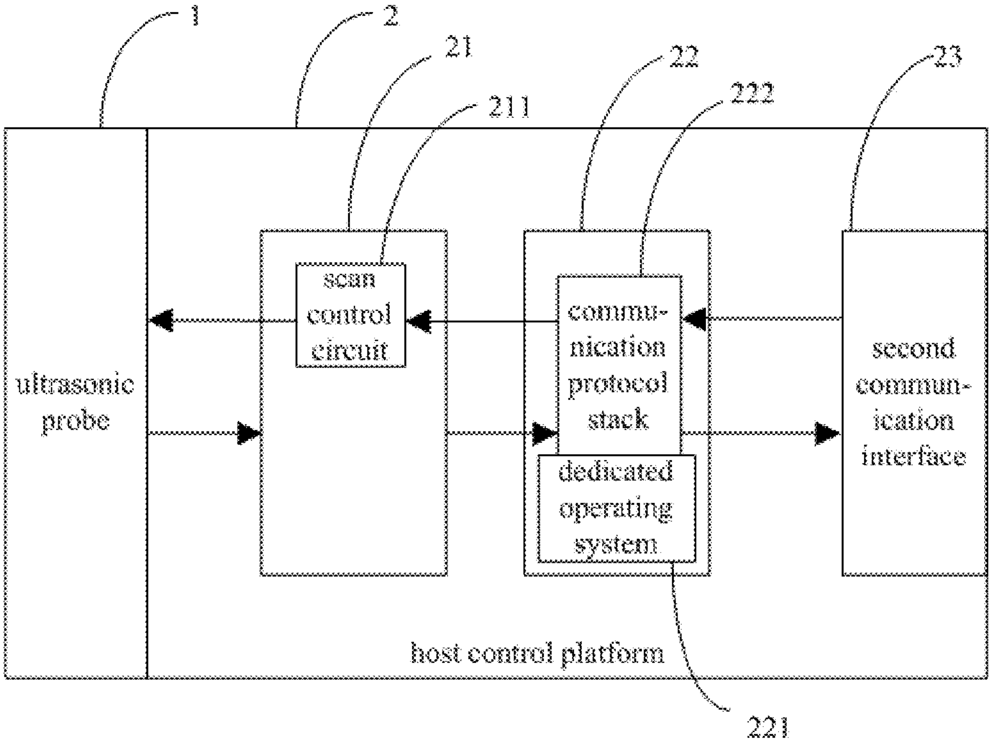
FIG. 3 is a block diagram of an ultrasonic probe and a host control platform according to some embodiments.

Please refer to FIG. 3. In the shown embodiment, the host control platform 2 may mainly include a programmable logic device 21, a controller 22 and a second communication interface 23. The programmable logic device 21, the controller 22 and the second communication interface 23 may be three independent physical hardware components, wherein the programmable logic device 21 may be a programmable logic chip, the controller 22 may be a dedicated control chip, and the second communication interface 23 may be a communication interface chip.

The second communication interface 23 may be capable of establishing a communication connection with the first communication interface of the terminal device 3. This communication connection may be either a wired or wireless connection.

The programmable logic device 21 may include a scan control circuit 211 that is communicatively connected to the ultrasonic probe 1. The scan control circuit 211 may be configured to control the ultrasonic probe to emit ultrasonic waves to the object under examination and receive ultrasonic echoes, so as to obtain ultrasonic echo signal. The scan control circuit 211 may receive the imaging scanning instruction sent by the terminal device 3 via the second communication interface 23, and according to the received imaging scanning instruction, control the ultrasonic probe 1 to emit ultrasonic waves and receive ultrasonic echoes.

The controller 22 may be deployed with a dedicated operating system 221 and a communication protocol stack 222. The controller 22 may be communicatively connected to the programmable logic device 21. The dedicated operating system 221 may be a simplified operating system that is configured to control the communication between the programmable logic device 21 and the terminal device 3. The dedicated operating system 221 may control the programmable logic device 21 to receive the imaging scanning instruction sent by the terminal device 3. The communication protocol stack 222 may be a communication protocol stack that is compatible with the second communication interface 23, and may be configured to package and unpack data.

The dedicated operating system 221 may be configured to obtain the ultrasonic data from the programmable logic device 21, invoke the communication protocol stack 222 to convert the ultrasonic data into packet data that conforms to the communication protocol stack corresponding to the first communication interface 31, and transmit the packet data to the terminal device 3 via the second communication interface.

In the shown embodiment, the working principle of the ultrasonic imaging system is as follows:

The terminal device 3 transmits an imaging scanning instruction to the host control platform 2 via the first communication interface 31. Optionally, the terminal device 3 may packet the imaging scanning instruction to the host control platform 2.

The host control platform 2 receives the imaging scanning instruction via the second communication interface 23, the dedicated operating system 221 controls the programmable logic device 21 to obtain the imaging scanning instruction received by the second communication interface 23. When the imaging scanning instruction has been packaged, the communication protocol stack 222 may first unpack the packed imaging scanning instruction before sending them to the programmable logic device 21.

The scan control circuit 211 in the programmable logic device 21, according to the imaging scanning instruction, controls the ultrasonic probe 1 to emit ultrasonic waves and receive ultrasonic echoes so as to obtain ultrasonic data.

The programmable logic device 21 directly transmits the obtained ultrasonic data to the controller 22, the dedicated operating system 221 of the controller 22 obtains the ultrasonic data, invokes the communication protocol stack 222 to convert the ultrasonic data into packet data that conforms to the communication protocol corresponding to the communication protocol stack that is compatible with the first communication interface 31, and transmit the packet data to the terminal device 3 via the second communication interface 23.

The terminal device 3 receives the packet data sent by the host control platform 2 via the first communication interface 31, and then unpacks the packet data and performs image processing to ultimately obtain ultrasonic image data.

Finally, the terminal device 3 controls a display to show the obtained ultrasonic image, thus completing the detection of the ultrasonic image. The detection of the ultrasonic image is a continuous dynamic detection. The terminal device 3 may transmit imaging scanning instructions at intervals. The ultrasonic probe 1 may continuously transmit and receive ultrasonic waves, and the host control platform 2 may continuously transmit the ultrasonic data to the terminal device 3.

In the shown embodiment, the primary function of the programmable logic device 21 is to control the ultrasonic probe 1 to emit ultrasonic waves and receive ultrasonic echoes, the primary function of the controller 22 is to packet and unpack data, and the host control platform 2 configures the communication protocol stack used for data packing and unpacking into the controller 22. The communication protocol stack is independent of the programmable logic device 21 that may be without an ARM core or without a deployed protocol stack. This simplifies the functions of the programmable logic device 21. The programmable logic device 21 may be an FPGA (Field Programmable Gate Array), and a conventional FPGA can be selected for use as the programmable logic device 21.

In the shown embodiment, the host control platform 2 directly packages the ultrasonic data generated by the ultrasonic probe 1 and sends the packed data to the terminal device 3, and the terminal device 3 processes the ultrasonic data to obtain an ultrasonic image. This simplifies the functions of the host control platform 2, allowing for further miniaturization of the host control platform 2 and low-power operations of the host control platform 2. Accordingly, the heat generated by the host control platform 2 can be reduced, and the operational time of the host control platform 2 can be extended, thus improving the user experience when holding or carrying the host control platform 2.

In the shown embodiment, the host control platform 2 can connect to one or more terminal devices 3 simultaneously. For example, the host control platform 2 can connect to two terminal devices 3 at the same time: one being a smartphone and the other a cloud server. Ultrasonic imaging detection can be performed by directly connecting the host control platform 2 to the ultrasonic probe 1 via the smartphone. Meanwhile, the host control platform 2 uploads data to the cloud server for backup, enabling the preservation and recording ultrasonic detection data. This can prevent the loss of past ultrasonic detection data due to damage to the smartphone.

The ultrasonic imaging system in this embodiment also encompasses the following advantages:

(1) minimal constraints on the selection of the programmable logic device 21: by making the communication protocol stack 222 independent of the programmable logic device 21, it is unnecessary for the programmable logic device 21 to be incorporated with the communication protocol stack, allowing for the use of conventional FPGAs;

(2) improved design decoupling: it is achieved as the programmable logic device 21 and the controller 22 are interconnected through the dedicated operating system. Maintaining this interconnection allows for changes (e.g. adding or reducing a functional module) within either the programmable logic device or the controller without affecting the functional operation of each other;

(3) Enhanced scalability: when the ultrasonic imaging system needs to improve its imaging performance, a programmable logic device with higher performance (i.e. a higher-performance FPGA) can be replaced independently; and similarly, when there are changes or new requirements for the communication interfaces, the first and second communication interfaces can be replaced independently; and (4) reduced power consumption: during the freeze period of ultrasonic imaging (the period when the transmission and reception of ultrasonic waves are disable), the controller maintains communication with external devices, while the programmable logic device does not need to maintain communication continuously. This allows the programmable logic device to be in a standby state with lower power consumption, and it can be restored to normal operation when ultrasonic imaging scanning is carried out.

In some embodiments, the communication protocol stack 222 of the controller 22 in the host control platform 2 may include a TCP protocol stack and a WIFI protocol stack; and the first communication interface 31 of the terminal device 3 may include corresponding TCP and WIFI protocol stacks, enabling communication between the host control platform 2 and the terminal device 3 via the TCP and WIFI protocol stacks. The WIFI protocol stack facilitates remote wireless data transmission, allowing the host control platform 2 to communicate with the terminal device 3 (such as a cloud server, an ultrasonic imaging device, etc.) via the WIFI protocol stack.

In some embodiments, the communication protocol stack 222 of the controller 22 in the host control platform 2 may include a TCP protocol stack and a Bluetooth protocol stack; and the first communication interface 31 of the terminal device 3 may include corresponding TCP and Bluetooth protocol stacks, enabling communication between the host control platform 2 and the terminal device 3 via the TCP and Bluetooth protocol stacks. The Bluetooth protocol stack enables short-range wireless data transmission, allowing the host control platform 2 to communicate with the terminal device 3 (such as a smartphone, a tablet computer, etc.) via the Bluetooth protocol stack.

In some embodiments, the communication protocol stack 222 of the controller 22 in the host control platform 2 may include a USB protocol stack; and the first communication interface 31 of the terminal device 3 may include a corresponding USB protocol stack, enabling communication between the host control platform 2 and the terminal device 3 via the USB protocol stack. The USB protocol stack enables short-range wired data transmission, allowing the host control platform 2 to communicate with the terminal device 3 (such as a smartphone, a tablet computer, an ultrasonic imaging device, etc.) via the USB protocol stack.

In some embodiments, the communication protocol stack 222 of the controller 22 in the host control platform 2 may include at least two of a TCP protocol stack, a WIFI protocol stack, a Bluetooth protocol stack and a USB protocol stack. For example, the communication protocol stack 222 includes a TCP protocol stack, a WIFI protocol stack, a Bluetooth protocol stack and a USB protocol stack; and the first communication interface 31 of the terminal device 3 supports a protocol stack corresponding to the second communication interface 23. The host control platform 2 can choose to communicate with the terminal device 3 using remote wireless data transmission, short-range wireless data transmission and wired transmission, allowing users to select a protocol stack for data transmission based on the available terminal device 3.

In some embodiments, the communication protocol stack may include SPI (Serial Peripheral Interface) protocol stack, SDIO (Secure Digital Input and Output) protocol stack, RMII (Reduced Media Independent Interface) protocol stack and/or any other suitable protocol stack.

In some embodiments, the second communication interface 23 of the host control platform 2 may include at least one of a WIFI communication interface, a Bluetooth communication interface, a SPI communication interface, a SDIO communication interface, a RMII communication interface and a USB communication interface; and the second communication interface 23 corresponds to the communication protocol stack 222. For example, when the communication protocol stack 222 includes the WIFI protocol stack, the second communication interface 23 is correspondingly configured with the WIFI communication interface. Similarly, the first communication interface 31 has the same type of communication interface as the second communication interface 23, to enable wired or wireless communication between the first communication interface 31 and the second communication interface 23.

When the communication protocol stack 222 includes a USB protocol stack, the first communication interface 31 and the second communication interface 23 include a USB communication interface, the USB communication interface supports a control transfer mode, an interrupt transfer mode, a bulk transfer mode and an isochronous transfer mode. The bulk transfer mode and the isochronous transfer mode are suitable for transmitting large-scale and real-time data. The packet data sent from the host control platform 2 to the terminal device 3 belongs to large-scale imaging data; accordingly, the USB communication interface of the host control platform 2 can employ the bulk transfer mode or the isochronous transfer mode to transmit packet data to the terminal device 3. The control transfer mode and the interrupt transfer mode are suitable for small-scale and non-real-time data. The imaging scanning instructions send by the terminal device 3 to the host control platform 2 belongs to small-scale and non-real-time data; hence, the USB communication interface of the terminal device 3 can utilize the control transfer mode or the interrupt transfer mode to transmit the imaging scanning instructions to the host control platform 2.

In some embodiment, the second communication interface 23 may include a port physical layer (PHY layer) (not shown). In some embodiment, the second communication interface 23 or the PHY layer may be integrated with the controller 22, such as integrated in the controller 22 or integrated on the controller. This way, the area occupied by the controller and the second communication interface can be reduced, thereby helping to reduce the volume of the ultrasonic imaging system or the host control platform.

Figure 4:
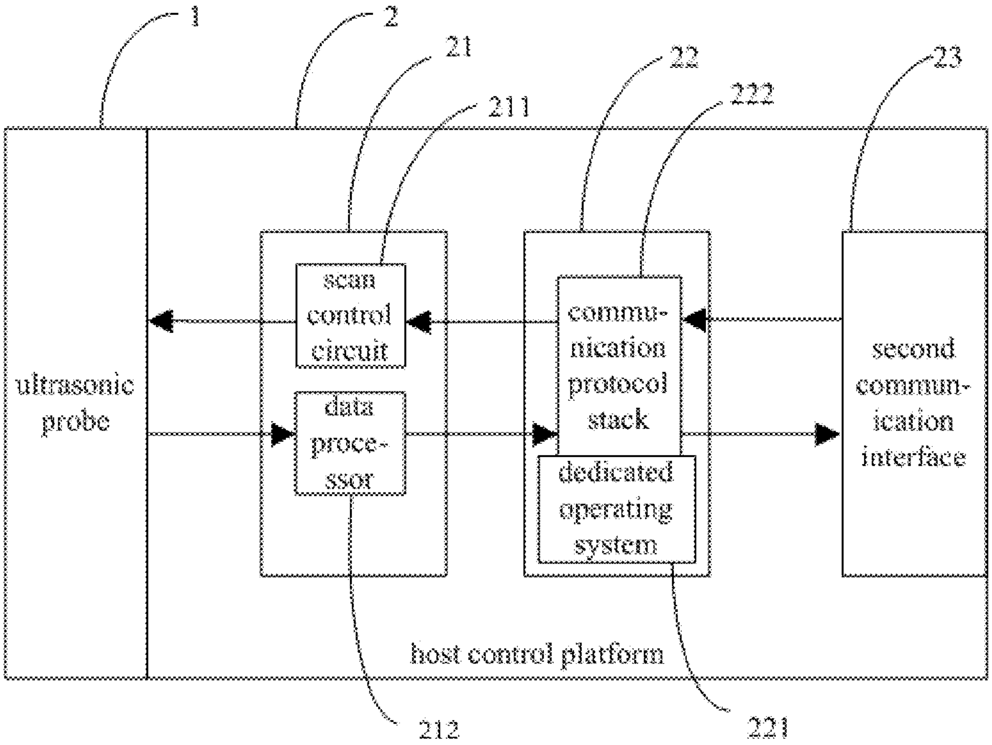
FIG. 4 is a block diagram of an ultrasonic probe and a host control platform according to some embodiments.
Figure 5:
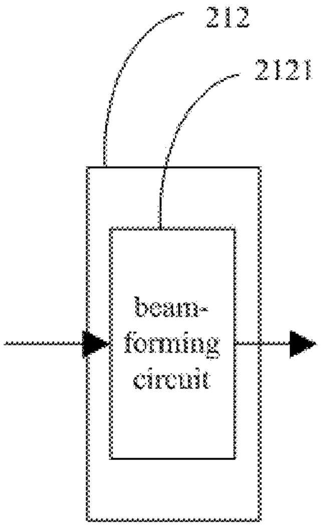
FIG. 5 is a block diagram of a data processor according to some embodiments.

Please refer to FIG. 4 and FIG. 5. In some embodiments, the host control platform 2 may preprocess the ultrasonic data before transmitting it to the terminal device 3. The programmable logic device 21 of the host control platform 2 may further include a data processor 212 configured to process the ultrasonic data.

The data processor 212 may include a beamforming circuit 2121 configured to perform at least partial beamforming on the ultrasonic echo signals. When the ultrasonic probe 1 emits ultrasonic waves, it does so through a plurality of element array transmitters, emitting a plurality of beams of ultrasonic waves. The ultrasonic echoes received by the ultrasonic probe 1 also include a plurality of beams of ultrasonic waves; therefore, the ultrasonic data include data from a plurality of beams of ultrasonic waves. The beamforming circuit 2121 may process and combine a portion of the data within the ultrasonic data. For example, the beamforming circuit 2121 may beamform all of the data in the ultrasonic data. The beamforming process performed by the beamforming circuit 2121 helps to improve the stability of the ultrasonic data, and the host control platform 2 transmits the beamformed ultrasonic data to the terminal device, which improves the final imaging quality.

Figure 6:
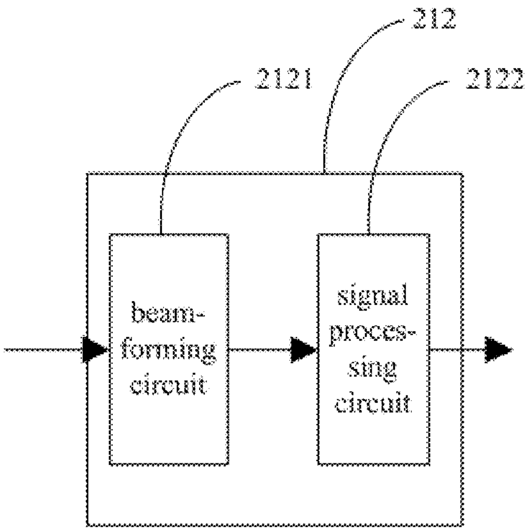
FIG. 6 is a block diagram of a data processor according to some embodiments.

Please refer to FIG. 4 and FIG. 6. In the shown embodiments, the data processor 212 includes a beamforming circuit 2121 and a signal processing circuit 2122. After the beamforming circuit 2121 performs at least partial beamforming on the ultrasonic data, the signal processing circuit 2122 processes the beamformed ultrasonic data to obtain an ultrasonic image. This allows the ultrasonic data sent by the host control platform 2 to the terminal device 3 to be displayed, meaning that part of the processing for imaging the ultrasonic data, originally performed by the terminal device 3, is transferred to the host control platform 2 for implementation. This reduces the functional requirements of the terminal device 3, enabling even terminal devices 3 with lower-end processors to be connected and used with the host control platform 2.

Figure 7:
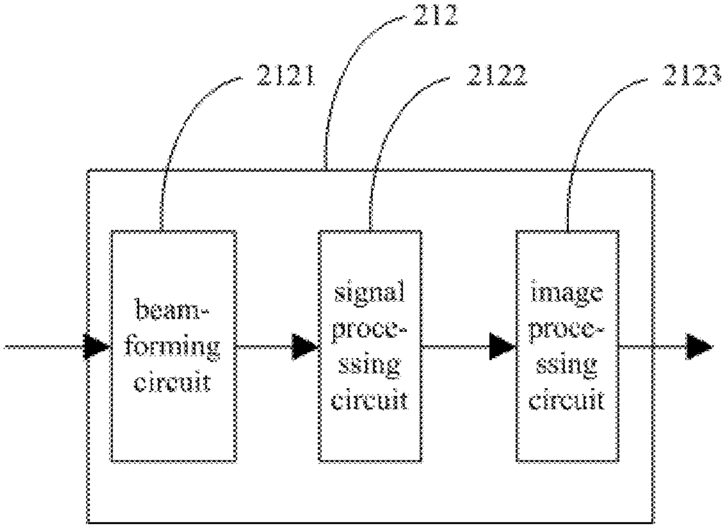
FIG. 7 is a block diagram of a data processor according to some embodiments.

Please refer to FIG. 4 and FIG. 7. In the shown embodiments, the data processor 212 includes a beamforming circuit 2121, a signal processing circuit 2122 and an image processing circuit 2123. After the beamforming circuit 2121 performs at least partial beamforming on the ultrasonic data, the signal processing circuit 2122 processes the beamformed ultrasonic data to obtain an ultrasonic image. The image processing circuit 2123 may process the obtained ultrasonic image, so that the ultrasonic data sent by the host control platform 2 to the terminal device 3 can be displayed directly, which means that all of the processing for imaging the ultrasonic data, originally performed by the terminal device 3, is transferred to the host control platform 2 for implementation. This facilitates direct connection and use of the terminal devices 3 such as tablet computers and tablets with the host control platform 2.

Figure 8:
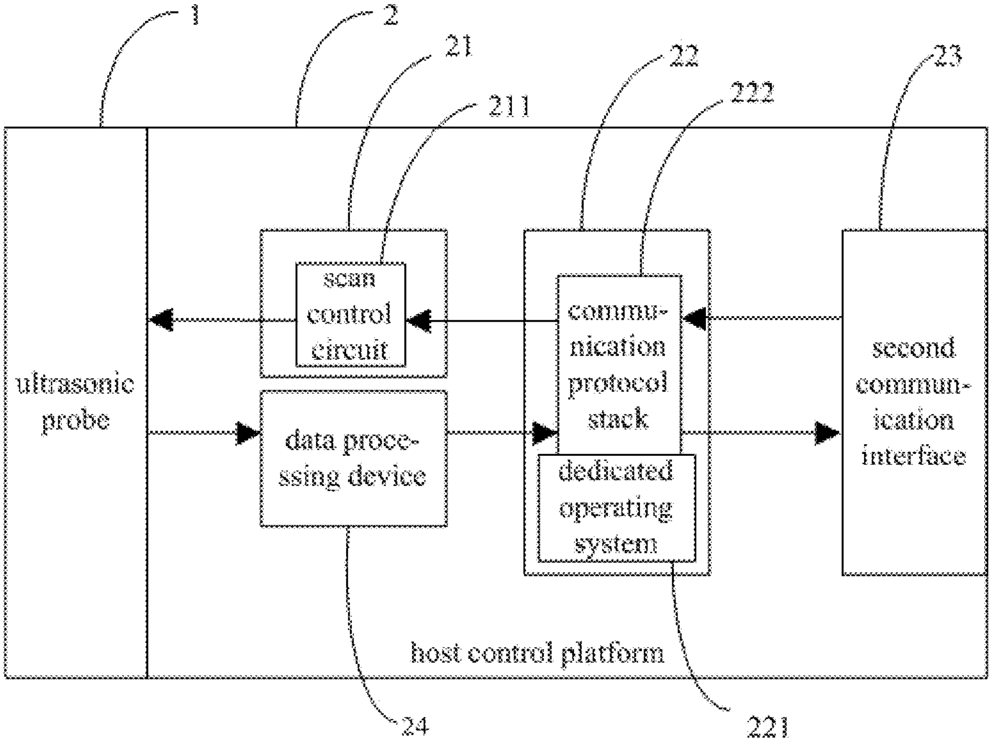
FIG. 8 is a block diagram of an ultrasonic probe and a host control platform according to some embodiments.
Figure 9:
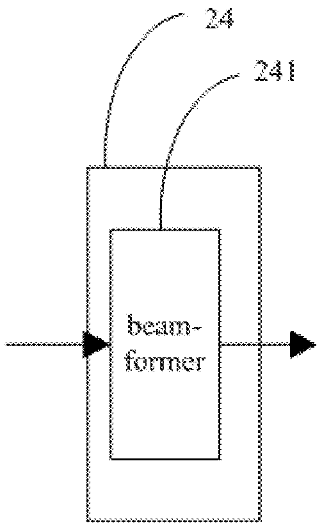
FIG. 9 is a block diagram of a data processing device according to some embodiments.

Please refer to FIG. 8 and FIG. 9. In the shown embodiments, the host control platform 2 can preprocess the ultrasonic data before sending it to the terminal device 3. The host control platform 2 further includes a data processing device 24 for processing the ultrasonic data. The data processing device 24 is independent of the programmable logic device 21, which reduces the requirements for selecting the programmable logic device 21, and facilitates low-power operation of the programmable logic device 21 as well as its replacement with FPGAs of other performance levels. The data processing device 24 can be a circuit, a microprocessor, a GPU, or other devices, and it may be a single device or a combination of a plurality of devices.

The data processing device 24 includes a beamformer 241 for performing at least partial beamforming on the ultrasonic echo signals. The beamformer 241 may be provided inside with a beamforming processing unit, and the beamformer 241 can perform beamforming on the ultrasonic echo signals through software. The beamformer 241 may also include a beamforming processing device, and the beamformer 241 can perform beamforming on the ultrasonic echo signals through hardware. When the ultrasonic probe 1 emits ultrasonic waves, it does so through a plurality of element array transmitters, emitting a plurality of beams of ultrasonic waves. The ultrasonic echoes received by the ultrasonic probe 1 also include a plurality of ultrasonic waves; therefore, the ultrasonic data includes data from a plurality of beams of ultrasonic waves. The beamformer 241 performs beamforming on part of the ultrasonic data; for example, it performs beamforming on all of the ultrasonic data. The beamforming process carried out by the beamformer 241 helps improve the stability of transmission of the ultrasonic data; and the host control platform 2 transmitting the beamformed ultrasonic data to the terminal device contributes to enhancing the final imaging effect.

Figure 10:
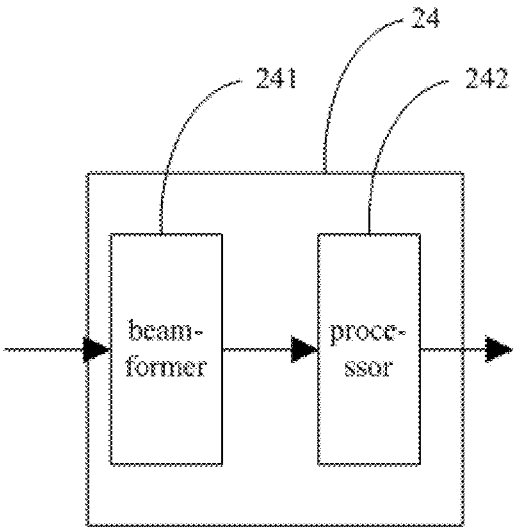
FIG. 10 is a block diagram of a data processing device according to some embodiments.

Please refer to FIG. 8 and FIG. 10. In the shown embodiments, the data processing device 24 includes a beamformer 241 and a processor 242. After the beamformer 241 performs at least partial beamforming on the ultrasonic data, the processor 242 process the beamformed ultrasonic data to obtain an ultrasonic image, so that the ultrasonic data sent by the host control platform 2 to the terminal device 3 can be directly displayed, meaning that part of the processing for imaging the ultrasonic data, originally performed by the terminal device 3 is transferred to the host control platform 2 for implementation. This reduces the functional requirements of the terminal device 3, enabling even terminal devices 3 with lower-end processors to be connected and used with the host control platform 2.

In some embodiments, the data processor 212 includes a beamformer 241 and a processor 242. After the beamformer 241 performs at least partial beamforming on the ultrasonic data, the processor 242 processes the beamformed ultrasonic data to obtain an ultrasonic image. The processor 242 may also process the obtained ultrasonic image. This enables the ultrasonic data sent by the host control platform 2 to the terminal device 3 to be directly displayed, meaning that all of the processing functionality for imaging the ultrasonic data, originally performed by the terminal device 3, is transferred to the host control platform 2 for implementation, thereby facilitating direct connection and use of the terminal devices 3 such as smartphones, tablet computers with the host control platform 2.

In some embodiments, an ultrasonic imaging system is provided, which differs from the ultrasonic imaging system described in the aforementioned embodiments in that it does not include the terminal device 3.

The ultrasonic imaging system in such embodiments includes a ultrasonic probe 1, a programmable logic device 21, a controller 22 and a second communication interface 23. The programmable logic device 21, the controller 22 and the second communication interface 23 can be directly mounted in the ultrasonic probe 1, or they can be mounted in a same host control platform.

The second communication interface 23 of this ultrasonic imaging system can be capable of establishing a communication connection with a target device that may be the terminal device 3 described in the aforementioned embodiments.

The target device communicatively connected to the second communication interface 23 of this ultrasonic imaging system may also be a component inside the ultrasonic imaging system. For example, a display screen is provided on the outer surface of the ultrasonic probe 1, and this display screen is the target device. The host control platform 2 is disposed in the ultrasonic probe 1, the second communication interface 23 of the host control platform 2 is communicatively connected to the display screen. The host control platform 2 processes the ultrasonic data to obtain an ultrasonic image, and then the host control platform 2 transmits the processed ultrasonic data via the second communication interface 23 to the display screen for direct display.

The target device communicatively connected to the second communication interface 23 of the ultrasonic imaging system may also be an external component of the ultrasonic imaging system. For example, there may be a dedicated device for displaying the ultrasonic image, which includes a processor and a display screen. Such device may also be provided with a first communication interface, and the second communication interface 23 of the host control platform 2 may transmit the ultrasonic data to this device. The device may then process the ultrasonic data and display the ultrasonic image.

In some embodiments, an ultrasonic imaging system is provided, which differs from the ultrasonic imaging system described in the aforementioned embodiments in that the hardware deployment of the scan control circuit 211, the controller 22 and the second communication interface 23 in this ultrasonic imaging system is different from that in the above embodiments.

In this embodiment, the ultrasonic imaging system includes an ultrasonic probe 1, a scan control circuit 211, a controller 22 and a second communication interface 23. For example, the scan control circuit 211 may be integrated into the controller 22, or it may be independently deployed on a chip different from a programmable logic device, The scan control circuit 211 may include a transmitting circuit and a receiving circuit. The scan control circuit 211 may control the ultrasonic probe 1 to emit ultrasonic waves via the transmitting circuit, and the scan control circuit 211 may obtain the ultrasonic data acquired by the ultrasonic probe 1 via the receiving circuit.

The second communication interface 23 of this ultrasonic imaging system is capable of establishing a communication connection with the target device that may be the terminal device 3 mentioned in the aforementioned embodiments.

The target device communicatively connected to the second communication interface 23 of this ultrasonic imaging system may also be a component inside the ultrasonic imaging system. For example, the ultrasonic probe 1 is provided on its outer surface with a display screen that is the target device. The host control platform 2 is disposed inside the ultrasonic probe 1, the second communication interface 23 of the host control platform 2 is communicatively connected to the display screen; and the host control platform 2 processes the ultrasonic data to obtain an ultrasonic image and then transmits the processed ultrasonic data to the display screen for direct display via the second communication interface 23.

The target device communicatively connected to the second communication interface 23 of the ultrasonic imaging system may also be an external component of the ultrasonic imaging system. For example, there may be a dedicated device for displaying the ultrasonic image, which includes a processor and a display screen. Such device may also be provided with a first communication interface, and the second communication interface 23 of the host control platform 2 may transmit the ultrasonic data to this device. The device may then process the ultrasonic data and display the ultrasonic image.

In some embodiments, the controller in the embodiments above may not be provided with a dedicated operating system. Instead, the controller may directly obtain the ultrasonic data from the programmable logic device, invoke the communication protocol stack to convert the ultrasonic data into packet data that conforms to a communication protocol corresponding to the communication protocol stack, and transmit the packet data to the terminal device via the second communication interface. Alternatively, in some embodiments, a conventional operating system may be provided in the controller, and the controller may, via the conventional operating system, obtain the ultrasonic data from the programmable logic device, invoke the communication protocol stack to convert the ultrasonic data into packet data that conforms to a communication protocol corresponding to the communication protocol stack, and transmit the packet data to the terminal device via the second communication interface.

For example, in one embodiment, the ultrasonic imaging system may include an ultrasonic probe, a terminal device and a host control platform. The terminal device may include a first communication interface. The host control platform may be configured to control the ultrasonic probe to emit ultrasonic waves to an object under examination and receive ultrasonic echoes to obtain ultrasonic data, and transmit the ultrasonic data to the terminal device.

The host control platform may include a programmable logic device, a second communication interface and a controller. The programmable logic device may include a scan control circuit that is configured to control the ultrasonic probe to emit the ultrasonic waves to the object under examination and receive the ultrasonic echoes to obtain the ultrasonic data. The second communication interface may be capable of establishing a communication connection with the first communication interface. The controller may be deployed with a communication protocol stack. The communication protocol stack is compatible with the second communication interface. The controller may be configured to obtain the ultrasonic data from the programmable logic device, invoke the communication protocol stack to convert the ultrasonic data into packet data that conforms to a communication protocol corresponding to the communication protocol stack, and transmit the packet data to the terminal device via the second communication interface.

In one embodiment, the ultrasonic imaging system may include an ultrasonic probe, a programmable logic device, a second communication interface and a controller.

The programmable logic device may include a scan control circuit that is configured to control the ultrasonic probe to emit ultrasonic waves to an object under examination and receive ultrasonic echoes so as to obtain ultrasonic data. The second communication interface may be capable of establishing a communication connection with a target device. The controller may be deployed with a communication protocol stack. The communication protocol stack is compatible with the second communication interface. The controller may be configured to obtain the ultrasonic data from the programmable logic device, invoke the communication protocol stack to convert the ultrasonic data into packet data that conforms to a communication protocol corresponding to the communication protocol stack, and transmit the packet data to the target device via the second communication interface.

In one embodiment, the ultrasonic imaging system may include an ultrasonic probe, a scan control circuit, a second communication interface and a controller.

The scan control circuit may be configured to control the ultrasonic probe to emit ultrasonic waves to an object under examination an receive ultrasonic echoes so as to obtain ultrasonic data. The second communication interface may be capable of establishing a communication connection with a target device. The controller may be deployed with a communication protocol stack. The communication protocol stack is compatible with the second communication interface. The controller may be configured to obtain the ultrasonic data from the scan control circuit, invoke the communication protocol stack to convert the ultrasonic data into packet data that conforms to a communication protocol corresponding to the communication protocol stack, and transmit the packet data to the target device via the second communication interface.

In one embodiment, the controller may be further deployed with an operating system, and the controller may obtain the ultrasonic data from the scan control circuit, invokes the communication protocol stack to convert the ultrasonic data into packet data that conforms to a communication protocol corresponding to the communication protocol stack, and transmits the packet data to the target device via the second communication interface through the operating system. The operating system may be a dedicated operating system, such as a simplified operating system for controlling the communication between the programmable logic device and the terminal device or the target device. Alternatively, the operating system may be a conventional operating system, such as a Linux operating system or a RTOS operating system.

In one embodiment, the second communication interface may include a port physical layer (PHY layer), and the second communication interface or the port physical layer may be integrated with the controller.

In some embodiments above, the programmable logic device and the controller are provided, the scan control circuit for controlling the ultrasonic probe to transmit and receive ultrasonic waves is provided in the programmable logic device, and the communication protocol stack is provided in the controller to obtain and transmit data packets. This way, the constraints on the selection of the programmable logic device are reduced. Furthermore, the communication protocol stack is independent of the programmable logic device. Therefore, the programmable logic device does not need to be provided with a communication protocol stack, which allow the use of a conventional FPGA.

In some embodiments above, there is a better design decoupling. The programmable logic device and the controller can be interconnected through the operating system. Maintaining this interconnection allows for changes within either the programmable logic device or the controller without affecting the functional operation of the other.

In some embodiments above, better expansion performance can be achieved. When the ultrasound imaging system needs to improve the imaging performance, a programmable logic device with higher performance can be replaced independently; and similarly, when there are changes or new requirements for the communication interfaces, the first and second communication interfaces can be replaced independently.

In some embodiments above, lower power consumption can be achieved. During the freezing period of ultrasound imaging, the controller can maintain an external communication connection, while the programmable logic device does not need to maintain communication all the time. Therefore, the programmable logic device can be in a low-power standby state, and can be restored to normal operation when the ultrasound imaging scan is performed.

The specific examples employed above to illustrate the present disclosure are for the purpose of facilitating understanding and are not intended to limit the invention. Those skilled in the art to which the present disclosure pertains, without departing from the basic principles of the present disclosure, may make various simple deductions, modifications or substitutions.

The invention claimed is:

1. An ultrasonic imaging system, comprising:

an ultrasonic probe;

a terminal device, comprising a first communication interface; and a host control platform, configured to control the ultrasonic probe to emit ultrasonic waves to an object under examination and receive ultrasonic echoes to obtain ultrasonic data, and transmit the ultrasonic data to the terminal device;

wherein the host control platform comprises:

a programmable logic device, comprising a scan control circuit that is configured to control the ultrasonic probe to emit the ultrasonic waves to the object under examination and receive the ultrasonic echoes to obtain the ultrasonic data;

a second communication interface, capable of establishing a communication connection with the first communication interface; and a controller, deployed with a dedicated operating system and a communication protocol stack, wherein, the dedicated operating system is a simplified operating system for controlling communication between the programmable logic device and the terminal device, the communication protocol stack is compatible with the second communication interface, and the dedicated operating system is configured to obtain the ultrasonic data from the programmable logic device, invoke the communication protocol stack to convert the ultrasonic data into packet data that conforms to a communication protocol corresponding to the communication protocol stack, and transmit the packet data to the terminal device via the second communication interface, wherein the programmable logic device and the controller are independent chips, and the programmable logic device is a programmable logic device without an ARM core or without a deployed protocol stack.

2. The ultrasonic imaging system of claim 1, wherein the communication protocol stack comprises a TCP protocol stack and a WIFI protocol stack; and/or the communication protocol stack comprises a TCP protocol stack and a Bluetooth protocol stack; and/or the communication protocol stack comprises a USB protocol stack; and/or the communication protocol stack comprises a SPI protocol stack; and/or the communication protocol stack comprises a SDIO protocol stack; and/or the communication protocol stack comprises a RMII protocol stack.

3. The ultrasonic imaging system of claim 1, wherein the second communication interface comprises at least one of a WIFI communication interface, a Bluetooth communication interface, a SPI communication interface, a SDIO communication interface, a RMII communication interface and a USB communication interface.

4. The ultrasonic imaging system of claim 3, wherein the USB communication interface supports a control transfer mode, an interrupt transfer mode, a bulk transfer mode and an isochronous transfer mode, and the USB communication interface transmits the packet data using the bulk transfer mode or the isochronous transfer mode.

5. The ultrasonic imaging system of claim 1, wherein the programmable logic device is an FPGA.

6. The ultrasonic imaging system of claim 1, wherein the host control platform is arranged within the ultrasonic probe; or the ultrasonic probe and the host control platform are integrated into a single structure; or the host control platform is provided with a socket, and the ultrasonic probe is detachably connected to the host control platform via the socket.

7. The ultrasonic imaging system of claim 1, wherein the host control platform is connected to the ultrasonic probe via a wired or wireless connection.

8. The ultrasonic imaging system of claim 1, wherein the terminal device comprises at least one of a smartphone, a tablet computer, a cloud server and an ultrasonic imaging apparatus.

9. The ultrasonic imaging system of claim 1, wherein the programmable logic device further comprises a data processing circuit that is configured to process the ultrasonic data.

10. The ultrasonic imaging system of claim 9, wherein, the data processing circuit comprises a beamforming circuit that is configured to perform at least partial beamforming on the ultrasonic data; or the data processing circuit comprises a beamforming circuit that is configured to perform at least partial beamforming on the ultrasonic data and a signal processing circuit that is configured to process the beamformed ultrasonic data to obtain an ultrasonic image; or the data processing circuit comprises a beamforming circuit that is configured to perform at least partial beamforming on the ultrasonic data, a signal processing circuit that is configured to process the beamformed ultrasonic data to obtain an ultrasonic image, and an image processing circuit that is configured to process the obtained ultrasonic image.

11. The ultrasonic imaging system of claim 1, wherein the host control platform further comprises a data processing device that is configured to process the ultrasonic data.

12. The ultrasonic imaging system of claim 11, wherein, the data processing device comprises a beamformer that is configured to perform at least partial beamforming on the ultrasonic data; or the data processing device comprises a beamformer that is configured to perform at least partial beamforming on the ultrasonic data and a processor that is configured to process the beamformed ultrasonic data to obtain an ultrasonic image; or the data processing device comprises a beamformer that is configured to perform at least partial beamforming on the ultrasonic data and a processor that is configured to process the beamformed ultrasonic data to obtain an ultrasonic image and process the obtained ultrasonic image.

13. The ultrasonic imaging system of claim 1, wherein the second communication interface comprises a port physical layer, wherein the second communication interface or the port physical layer is integrated with the controller.

14. An ultrasonic imaging system, comprising:

an ultrasonic probe;

a terminal device, including a first communication interface; and a host control platform, configured to control the ultrasonic probe to emit ultrasonic waves to an object under examination and receive ultrasonic echoes to obtain ultrasonic data, and transmit the ultrasonic data to the terminal device;

wherein, the host control platform comprises:

a programmable logic device, comprising a scan control circuit that is configured to control the ultrasonic probe to emit the ultrasonic waves to the object under examination and receive the ultrasonic echoes to obtain the ultrasonic data;

a second communication interface, capable of establishing a communication connection with the first communication interface; and a controller, deployed with a communication protocol stack, wherein, the communication protocol stack is compatible with the second communication interface, and the controller is configured to obtain the ultrasonic data from the programmable logic device, invoke the communication protocol stack to convert the ultrasonic data into packet data that conforms to a communication protocol corresponding to the communication protocol stack, and transmit the packet data to the terminal device via the second communication interface, wherein the programmable logic device and the controller are independent chips, and the programmable logic device is a programmable logic device without an ARM core or without a deployed protocol stack.

15. An ultrasonic imaging system, comprising:

an ultrasonic probe;

a programmable logic device, comprising a scan control circuit that is configured to control the ultrasonic probe to emit ultrasonic waves to an object under examination and receive ultrasonic echoes so as to obtain ultrasonic data;

a second communication interface, capable of establishing a communication connection with a target device; and a controller, deployed with a communication protocol stack, wherein, the communication protocol stack is compatible with the second communication interface, and the controller is configured to obtain the ultrasonic data from the programmable logic device, invoke the communication protocol stack to convert the ultrasonic data into packet data that conforms to a communication protocol corresponding to the communication protocol stack, and transmit the packet data to the target device via the second communication interface, wherein the programmable logic device and the controller are independent chips, and the programmable logic device is a programmable logic device without an ARM core or without a deployed protocol stack.

16. The ultrasonic imaging system of claim 15, wherein, the controller is further deployed with an operating system, and the controller obtains the ultrasonic data from the scan control circuit, invokes the communication protocol stack to convert the ultrasonic data into packet data that conforms to a communication protocol corresponding to the communication protocol stack, and transmits the packet data to the target device via the second communication interface through the operating system.

17. The ultrasonic imaging system of claim 16, wherein the operating system is a Linux operating system or a RTOS operating system.

18. The ultrasonic imaging system of claim 15, wherein the second communication interface comprises a port physical layer, wherein the second communication interface or the port physical layer is integrated with the controller.

* * * * *